(12) United States Patent
Smith (10) Patent No.: US 7,867,508 B1
(45) Date of Patent: Jan. 11, 2011

(54) TREATMENT OF UPPER RESPIRATORY CONDITIONS

(76) Inventor: C. Steven Smith, 312 S. Lyndon La., Louisville, KY (US) 40222

( * ) Notice: Subject to any disclaimer, the term of this patent is extended or adjusted under 35 U.S.C. 154(b) by 37 days.

(21) Appl. No.: 11/829,119

(22) Filed: Jul. 27, 2007

Related U.S. Application Data (63) Continuation of application No. 10/660,841, filed on Sep. 12, 2003, now abandoned.

(51) Int. Cl.
*A61F 13/00* (2006.01)
*A61K 31/56* (2006.01)

(52) U.S. Cl. ........................ 424/434; 514/171

(58) Field of Classification Search ............... None
See application file for complete search history.

(56) References Cited

U.S. PATENT DOCUMENTS

| | | | |
|---|---|---|---|
| 5,698,558 A * | 12/1997 | Gray | |
| 5,889,015 A * | 3/1999 | Sequeira et al. | |
| 6,344,210 B2 * | 2/2002 | Fust | |
| 6,777,441 B2 * | 8/2004 | Wang et al. | 514/475 |
| 2002/0061281 A1 * | 5/2002 | Osbakken et al. | |

OTHER PUBLICATIONS

Black et al. (1980) "Rhinitis Medicamentosa" CMA Journal vol. 122; pp. 881-884.*

William Storms (2007) "Allergic rhinitis-induced nasal congestion: its impact on sleep quality" Primary Care Respiratory Journal; 17(1); pp. 7-18.*

Dr. James Thompson "Nasal Spray Addiction-Know the Facts and Avoid the Danger" My Allergy Network.com, (2008).*

* cited by examiner

*Primary Examiner*—Humera N Sheikh
(74) *Attorney, Agent, or Firm*—Stites & Harbinson, PLLC; Mandy Wilson Decker (57) ABSTRACT

Provided are compositions and methods useful for the non-addictive treatment and prevention of upper respiratory conditions in man and animals, e.g., allergic, non-allergic and mixed rhinitis in man or pharyngitis and IAD in horses. Compositions of the invention comprise effective amounts of a suitable nasal decongestant; a suitable corticosteroid; and a suitable anticholinergic agent. The compositions and methods provided are especially useful for long term use in patients with mixed rhinitis and substantially reduce or eliminate the risk of rhinitis medicamentosa. The compositions and methods of treatment provided also eliminate the risk of adverse sequella seen from therapeutic regimens which employ systemic use of decongestants. The compositions provided can further comprise a suitable aromatic and/or a suitable antihistamine and can also comprise optional suitable antimicrobials, cytokine modulators, leukotriene antagonists, cromolyn sodium, or a suitable NDAID agent.

26 Claims, 1 Drawing Sheet

Figure 1

TREATMENT OF UPPER RESPIRATORY CONDITIONS

RELATED APPLICATION

This application is a continuation of U.S. patent application Ser. No. 10/660,841 filed Sep. 12, 2003 now abandoned.

TECHNICAL FIELD

The present invention generally relates to the treatment and/or prevention of upper respiratory pathology and/or disease in humans (and other susceptible animals). In particular, the present invention relates to novel compositions, for the acute treatment and also the long term treatment and/or prevention of mixed rhinitis in man and in animals which does not predispose the patient to development of rhinitis medicamentosa.

BACKGROUND

Rhinitis is a term used to describe the symptom complex related to irritation and inflammation of the nasal passageways (see, e.g., Middleton's Allergy Principles & Practice Volume II Fifth Edition Copyright 1998). Rhinitis affects 50 to 60 million Americans and the prevalence of allergic rhinitis has increased dramatically over the past 30 years.

Patients with rhinitis can experience a variety of symptoms including sneezing, rhinorrhea, nasal itching, congestion, and/or postnasal drainage. As a result, patients with these symptoms often experience headaches, fatigue, impaired concentration, reduced productivity, loss of sleep, increased occupational risk, increase in asthma, sinusitis, and otitis, and decreased emotional well being and social functioning (see, e.g., "Advice From Your Allergist" published by American College of Allergy, Asthma & Immunology, revised July 2000). Occasionally, children with chronic rhinitis develop altered facial growth and orthodontic problems. (See Table 1).

TABLE 1

Symptoms and Complications of Rhinitis

Symptoms

Rhinorrhea
Nasal congestion
Sneezing
Pruritus
Postnasal drip
Additional Symptoms Headache
Fatigue
Cognitive impairment
Complications Disturbances of facial growth and development
Dental malocclusions
Otitis media
Sinusitis
Disturbance of taste and smell
Sleep apnea and sleep interruption
Activation of nasal-bronchial reflexes Table Source: "Clinician's Manual on Rhinitis: Both Allergic and Nonallergic", Published by Science Press, Copyright 2001

The financial impact is also very significant. Health care expenditures in 1996 were estimated to be 6 billion dollars and this figure does not include the indirect cost of the 3.5 million loss work days and 2 million loss school days (See, Tables 2-3).

TABLE 2

Direct and Indirect Cost Estimates for Allergic Rhinitis (1994)

| Direct Costs | |
|---|---:|
| Ambulatory visits | 301,371,342 |
| Emergency department | 17,730,879 |
| Total Direct Costs | $1,147,258,636 |
| Office and clinic | 648,341,417 |
| Hospital outpatient | 179,814,998 |
| Indirect Costs | |
| Work-associated productivity loss | 46,793,667 |
| School-associated productivity loss | 16,656,697 |
| Restricted-activity-associated productivity loss | 22,959,642 |
| Total Indirect Costs | $ 86,410,006 |
| Total Costs | $1,233,668,642 |

Table Source: Clinician's Manual on Rhinitis: Both Allergic and Nonallergic, Published by Science Press, Copyright 2001

TABLE 3

Medical Expenditures Attributable to Allergic Rhinitis/Conjuctivitis and Related Airway Disorders (1996 US$/Millions)

| | | | | | | | |
|---|---:|---:|---:|---:|---:|---:|---:|
| Allergic rhinitis/conjunctivitis | § | 937.1 | 260.5 | § | 72.6 | 593.2 | 1863.4 |
| Chronic otitis media and eustachian tube disorder | 49.6 | 540.1 | 232.8 | 14.7 | 326.4 | 320.2 | 1483.5 |
| Sinusitis | 88.2 | 436.0 | 117.1 | 3.0 | 78.3 | 294.6 | 1017.3 |
| Asthma | 523.4 | 156.3 | 84.4 | § | 86.0 | 156.5 | 1006.7 |
| Acute upper respiratory infection | 12.8 | 82.3 | 30.7 | § | 36.4 | 49.1 | 211.8 |
| Phyaryngitis and tonsilitis | 7.8 | 63.7 | 21.4 | 0.1 | 36.8 | 35.9 | 165.7 |
| Other conjunctivitis | § | 33.2 | 16.0 | 0.3 | 20.3 | 18.2 | 88.0 |
| Chronic rhinitis | § | 30.1 | 8.9 | § | 3.7 | 19.6 | 62.3 |
| Rhinorrhea | § | 19.7 | § | 1.0 | § | 11.4 | 32.0 |
| TOTAL | 681.8 | 2299.0 | 771.8 | 19.1 | 660.5 | 1498.5 | 5930.7 |

*Included prescribed and over-the-counter medications ordered during visits to the physician's office, hospital outpatient department or emergency department. Did not include refills. § Nonsignificant expenditures according to criteria of the National Center for Health Statistics. Table Source: "Clinician's Manual on Rhinitis: Both Allergic and Nonallergic ", Published by Science Press, Copyright 2001

Chronic rhinitis, (rhinitis of greater than 6 weeks duration), is among the most common problem presenting to primary care physicians. Rhinitis can be caused by an allergy to inhalants, i.e., pollen, mold, animal dander and allergy to foods (58 million Americans). Non-allergic causes including strong odors, sudden temperature changes, alcohol ingestion, airborne irritants, skiing/jogging, pregnancy, spicy foods, and certain medications (e.g., topical agents such as certain alpha-adrenergic vasoconstrictors, cocaine, eye drops and oral agents such as antihypertensives, birth control pills, and certain phenothiazines) affect approximately 19 million Americans. Forty-four percent of the patients with allergic rhinitis have concomitant non-allergic rhinitis. This later group of patients with mixed rhinitis represents an estimated 26 million people in the United States. Prior to the present invention, however, there has not been an effective single entity medication for treatment and/or prevention of mixed rhinitis in patients.

Figure 1:
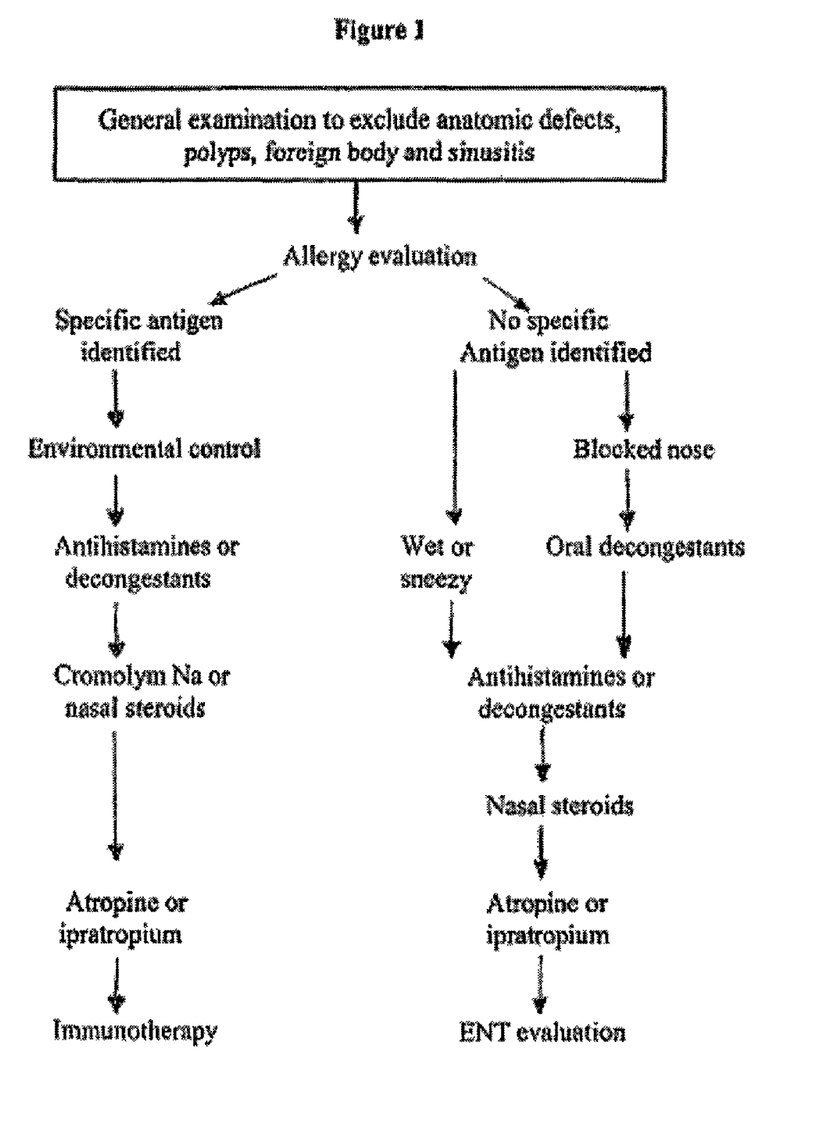
FIG. 1 flowchart is useful in establishing a pattern for pharmacologic therapy for mixed rhinitis.

The attached flowchart (See, FIG. 1) is useful in establishing a pattern for pharmacologic therapy for mixed rhinitis, which embraces an integrated approach (Figure Source: "Middleton's Allergy Principles & Practice", Vol. n, 5111 Edition, Copyright 1998). Currently, there are many single entry topical medications for treatment of allergic rhinitis. Nasal steroids, which top the list, (See, Table 5 below) help both the immediate and late phase response by modulating the production and effects of the ever-growing family of cytokines. Recently, cytokines have been shown to playa role in non-allergic rhinitis pathophysiology as well.

The diagnosis of mixed rhinitis is made when patients are known to have allergic rhinitis but their symptoms are clearly worsened by non-allergic triggers. Mixed rhinitis is one of the more difficult entities to treat, probably because of the great variety of provocative stimuli and its unremittingly perennial nature. Patients with mixed rhinitis can also already have an iatrogenic addiction to topical decongestants (rhinitis medicamentosa), chronic sinusitis, and/or nasal polyps as a result of their long-standing illness.

Empiric treatment with a topical broad based agent that is indicated for allergic rhinitis and non allergic rhinitis is a reasonable choice for first line therapy, but most patients need immediate relief of their symptoms to reinforce their long term plan with short term relief (see, e.g., Clinician's Manual on Rhinitis: Both Allergic and Nonallergic, published by Science Press, Copyright 2001). Topical decongestants fit this need, but used alone, they can induce rhinitis medicamentosa (iatrogenic rhinitis). Botanical agents which cool the nasal membranes such as menthol, camphor and eucalyptus give an immediate sensation of improved airflow. Interestingly, this sensation occurs without any actual change in nasal airway diameter or restriction. Thus, there is a subjective feeling of improvement with immediate results from the patient's perspective gives the patient the "security" of being able to breathe more easily (see, e.g., "Asthma and Rhinitis" edited by William W. Busse, & Stephen T. Holgate, published by Blackwell Science, Copyright 1995).

When it is not possible to definitively diagnose the type of rhinitis present (i.e., allergic vs. non-allergic), emphasis on broad based treatment should be considered. At present all of these broad based treatment components are available only as single entity formulations, i.e., single entity topical steroids, single entity topical decongestants (some with cooling aromatic components), single entity topical antihistamines or topical anticholinergic agents. Thus, there is a need in the art for a fixed integrated pharmacotherapy composition which can effectively treat the allergic as well as the non-allergic components of mixed rhinitis without harmful sequella, e.g., rhinitis medicamentosa. Prior to the present invention there had been no formulation useful for treatment of acute mixed rhinitis which combined effective amounts of a suitable nasal decongestant and a suitable corticosteroid that can also be used on a long term basis without inducing long term use complications such as rhinitis medicamentosa. The cost and compliance benefits of a such a composition are also of undeniable importance.

Presently, when long-term decongestant use is indicated, physicians must rely on systemic decongestants to avoid the adverse effects of long term topical use. Systemic therapy with decongestants can also produce adverse effects including; nervousness, insomnia, irritability headache, palpitations, tachycardia, hypertension, glaucoma, and decreased urinary flow as well as sexual dysfunction in males which greatly limits the use of oral decongestants. One of the only three alpha-adrenergic agonists available, phenylpropanolomine, was recently removed from the market because of fatal cardiovascular events related to its use, further limiting this choice of therapy. With only two systemic decongestants left, the therapy dilemma is even more complicated. Accordingly, there is a need in the art for a topical composition (as provided by the present invention) which can immediately alleviate congestion and can also be used on a long term basis without the risk of developing rhinitis medicamentosa or the risk adverse effects encountered with systemic decongestant therapy. The novel compositions provided by the present invention combine the use of topical nasal decongestant with an anti-inflammatory agent (topical steroid) and substantially eliminates the risk of rhinitis medicamentosa and concomitantly eliminates the risk of systemic decongestant use.

Likewise, in animals, especially companion animals such as dogs, cats and horses, there exists a need in the art for a composition adapted for topical administration and or nebulization which can effectively treat upper respiratory conditions in patients suffering from allergies, and/or infectious/inflammatory disorders such as inflammatory airway disease (IAD) and/or mixed rhinitis and that also can be used for treatment of lower respiratory conditions, e.g., recurrent airway obstruction (heaves). In horses, especially competition animals such as racing thoroughbreds, for example, inflammatory airway disease and/or upper respiratory inflammation can be troublesome and economically devastating. Pharyngitis, sinusitis and guttural pouch inflammation and/or infection if not properly treated can become a chronic manifestation in training animals and decrease performance. Inflammatory airway disease and pharyngitis or mixed rhinitis is often observed in young athletic horses, e.g., in two year olds in training. Mechanical irritation from breathing cold air in conjunction with environmental contaminants (dust, mold spores and the like) with or without an infectious component can predispose the animal to a lingering bout with upper airway inflammation such as pharyngitis or inflammatory airway disease. Clinical signs can be subtle and are often manifested as a chronic cough, excess mucus in the trachea and poor performance. Otherwise, the animal can have a normal attitude and appetite.

Treatment approaches to upper airway disease in the horse have largely been directed at treatment of the inflammation and broncho constriction which manifest especially with IAD. Aerosolized therapy with anti-inflammatory agents such as corticosteroids has been tried via nebulization or metered dose inhalation (MDI). In addition, bronchodilators such as albuterol have been used with some measure of success and also immunostimulants and antibiotic have been advocated. Treatment of pharangitis and gutteral pouch inflammation has been directed to various throat washes and lavages such as e.g., sodium iodide with or without DMSO. These can be used in conjunction with systemic antibiotic and or corticosteroid or other systemic anti-inflammatory agents such as NSAIDs, e.g., phenylbutazone or flunixin megulamine. However, prior to the present invention there has not been a single entity medication adapted for direct topical application which utilizes a unique combination of active agents for the effective treatment of upper airway disease in animals.

SUMMARY

The present invention provides compositions and methods useful for the non-addictive treatment and/or prevention of allergic, non-allergic and mixed rhinitis. In one embodiment, the compositions of the invention are comprised of effective amounts of a suitable nasal decongestant; a suitable synthetic or non-synthetic corticosteroid; and a suitable anticholinergic agent.

The compositions and methods provided by the invention can be used for relief of acute symptoms of allergic as well as non-allergic rhinitis, but are especially useful for long term use in patients with mixed rhinitis. The compositions and methods of the invention can be used for treatment and/or prevention of mixed rhinitis on a long term basis and substantially reduce or eliminate the risk of the patient developing rhinitis medicamentosa (e.g., as currently is frequently seen with long term use of the presently available topical nasal decongestant formulations). The compositions and methods of treatment provided by the invention also eliminate the risk of adverse sequella seen from therapeutic regimens which employ the systemic use of decongestants.

In one embodiment of the invention, the compositions provided can further comprise a suitable aromatic, e.g., a Botanical agent such as camphor, menthol or eucalyptus. Yet another embodiment of the invention, provides the compositions for treatment and/or prevention of allergic, non-allergic and/or mixed rhinitis which can further comprise an effective amount of a suitable antihistamine.

Another embodiment of the invention provides compositions comprised of effective amounts of a suitable nasal decongestant; a suitable corticosteroid; a suitable anticholinergic agent and a suitable antihistamine with or without the addition of a suitable aromatic agent. The core compositions of the invention comprised of a suitable nasal decongestant; a suitable corticosteroid and a suitable anticholinergic agent can further comprise optional suitable antimicrobials (antibiotics and/or antifungal and/or antiviral agents); cytokine modulators and/or inhibitors; leukotriene antagonists cromolyn sodium and/or a suitable NSAID agent.

The compositions of the invention are also useful for the long term treatment of sequella (e.g., constricted upper airway) in patients suffering from sleep apnea and receiving treatment with a constant positive pressure airway (CPAP) machine.

DESCRIPTION OF EXEMPLARY EMBODIMENTS

The present invention provides compositions and methods for the treatment and/or prevention of upper respiratory pathology and/or disease in man and in animals. The compositions provided herein can be used to treat and/or prevent any of a variety of upper respiratory conditions in man and animals including, but not limited to, allergic, non-allergic and mixed conditions having both allergic and non-allergic components (See, e.g., Table 4). In particular, the methods and compositions provided herein are useful in man for treatment and prevention of both acute and chronic manifestations of allergic, non-allergic and mixed rhinitis.

TABLE 4

| Differential Diagnosis of Rhinitis |
|---|
| Allergic Rhinitis |
| Seasonal<br>Perennial<br>Non-allergic Rhinitis<br>Vasomotor<br>NARES |

TABLE 4-continued

| Differential Diagnosis of Rhinitis |
|---|
| Rhinitis medicamentosa |
| Topical agents (alpha-adrenergic vasoconstrictors, cocaine, eye drops)<br>Oral agents (antihypertensives, birth control pills, phenothiazines)<br>Endocrine-induced |
| Pregnancy<br>Hypothyroidism<br>Acromegaly<br>Acute cholinergic-induced |
| Gustatory<br>Skier's/jogger's nose<br>Chronic sinusitis<br>Nasal polyposis<br>Anatomical obstruction |
| Tumors, granulomas, sarcoid<br>Wegener's<br>Septal deviation<br>Septal perforation<br>Cerebrospinal leakage<br>Atrophic<br>Mixed Rhinitis (allergic and non-allergic) |

Table Source: "Clinician's Manual on Rhinitis: Both Allergic and Nonallergic", Published by Science Press, Copyright 2001

In one embodiment, the compositions of the invention are adapted for topical, e.g., intranasal use and can be used in patients on a long term basis (for therapy of chronic or recurring upper respiratory conditions requiring daily or as needed, PRN, treatment) with a substantially reduced risk of adverse side effects such as rhinitis medicamentosa. Thus, the present invention also particularly provides methods of use for the novel compositions, for acute as well as long term treatment and/or prevention of upper respiratory conditions (e.g., mixed rhinitis in man and pharyngitis in animals) which does not predispose the patient to development of iatrogenic rhinitis (rhinitis medicamentosa).

In one embodiment, the present invention provides a composition that is useful for the non-addictive treatment and/or prevention of allergic, non-allergic and/or mixed rhinitis comprised of effective amounts of a suitable nasal decongestant; a suitable synthetic or non-synthetic corticosteroid; and a suitable anticholinergic agent. Examples of suitable nasal decongestants include, but are not limited to, any of a number of nasal decongestants that are currently used in prescription and over the counter preparations. Specific examples of suitable nasal decongestants include, but are not limited to, oxymetazoline, phenylephrine hydrochloride, phenylpropolamine hydrochloride, pseudophedrine and the like. Other examples of suitable decongestants (as well as other required agents, i.e., suitable corticosteroids and anticholinergic agents) that are adaptable for topical intranasal use can be found e.g., in Middleton, Elliott, Jr. et al., "Allergy Principles and Practice", 5th Ed., Volumes I & IT, Mosby-Year Book, Inc. (1988)) (ISBN 0-8151-0072-8) the contents of which are incorporated herein by reference in its entirety. (See also, The Physicians Desk Reference 56th Ed., Medical Economics, Inc. (2002) (ISBN: 156363-411-2) and also, The Physicians Desk Reference For Nonprescription Drugs And Dietary Supplements, 2151 Ed., Medical Economics, Inc. (2000) (ISBN: 156363-341-8) also incorporated herein by reference in their entirety).

Examples of suitable corticosteroids (or glucocorticosteroids) include, but are not limited to, betamethazone dipropionate, flunisolide, triamcinolone acetonide, fluticasone propionate, hydrocortisone, and the like. It is contemplated that any of the class of cortisone agents that are adaptable to localized (e.g., topical, intranasal) delivery can be utilized in the compositions set forth herein. (See Table 5 below) Anticholinegic agents which are suitable for use in the compositions provided by the present invention included, but are not limited to atropine, scopolomine, ipratropium bromide and the like.

TABLE 5

Intranasal Corticosteroids for Rhinitis Available in the United States

| Molecule | Trade Name | Formulation | Age (Years) | Dosage |
| --- | --- | --- | --- | --- |
| Beclomethasone | Beconase | MDI | 6-12 | 1 spray/nostril 3 ×/day |
| | Vancenase | | 12+ | 1 spray/nostril 2-4 ×/day |
| Belcomethasone | Beconase AQ, Vancenase AQ | Aqueous | 6+ | 1-2 spray/nostril 2 ×/day |
| Budesonide | Rhinocort | MDI | 6+* | 4 spray/nostril 1 ×/day or 2 spray/nostril 2 ×/day |
| Dexamethasone | Dexacort in | MD | 6-12 | 1-2 spray/nostril 2 ×/day |
| | Turbinaire ** | | 12+ | 2 spray/nostril 2/3 ×/day |
| Flunisolide | Nasarel | Solution | 6+ | 2 spray/nostril 2 ×/day or 1 spray/nostril 3 ×/day |
| Fluticasone | Flonase | Aqueous | 12+ | 2 spray/nostril once/day |
| Mometasone | Nasonex | Aqueous | 12+ | 2 spray/nostril once/day |
| Triamcinolone | Nasacort | MDI | 12+ | 2 spray/nostril once/day |
| Triamcinolone | Nasacort AQ | Aqueous | 6+ | 2 spray/nostril once/day |
| Triamcinolone | Trinasal | Solution | 6+ | 2 spray/nostril once/day |

MDI = Metered Dose Inhaler
"Reformulation of Nasalide with less propylene glycol
*Not recommended for perennial nonallergic rhinitis in children
**Indicated for "allergic or inflammatory nasal conditions and nasal polyps" Table Source: "Middleton's Allergy Principles & Practice", Vol. 11, 5th Edition, Copyright 1998

In general, it is preferable that the compositions of the invention be adapted for localized, e.g., intranasal delivery, with the active agents in a solution suitable for spraying or misting or other direct topical application. However, as can be appreciated, other variations such as powders and the like are possible and are within the scope of the invention. A presently preferred method of localized delivery of the compositions is via intranasal administration of a fine mist utilizing a standard metered dose pump, which can be calibrated to deliver an exact amount of the solution per administration, e.g., 0.1 ml per pump" It can also be appreciated that other forms of application are possible and are within the scope of the invention.

Given the many possible combinations of the required classes of active agents that are possible, it can be appreciated by one of skill in the art that the effective amount for any particular component of the compositions of the invention can vary depending upon the agent and/or the combination of agents selected, the condition being treated and the therapeutic regimen that is desired. However, given the teachings set forth herein one of skill in the art can optimize the effective amount of a given active agent given the identity of the other required agents of the combination for the compositions of the invention, the subject and condition being treated and the desired therapeutic regimen.

Thus, in one embodiment, a core combination of effective amounts of a suitable nasal decongestant; a suitable synthetic or non-synthetic corticosteroid; and a suitable anticholinergic agent are provided for the treatment of upper respiratory conditions in man and in animals. It is contemplated that other active agents can be added to the core compositions as desired. In particular, in another embodiment of the invention, the compositions for treatment and/or prevention of allergic, non-allergic and/or mixed rhinitis set forth above can further comprise an effective amount of a suitable aromatic agent such as e.g., camphor, eucalyptus, menthol or the like.

In another embodiment of the invention, the compositions for treatment and/or prevention of allergic, non-allergic and/or mixed rhinitis set forth above can further comprise an effective amount of a suitable antihistamine. Examples of suitable antihistamines include, but are not limited to, cetirizine, chlorpheniramine, diphenhydramine, dexchlorpheniramine, astemizole, azelastine, acrivastine, loratadine, terfenadine, cyproheptidine and the like.

Also contemplated by the present invention are the optional addition of suitable antibiotics and/or suitable antifungal agents and/or antiviral agents to the core compositions, as desired. The antibiotic and or antifungal agents can be selected from any of the currently available antimicrobial agents useful for treatment of upper respiratory infections. Examples of suitable antibiotics include any of the antibiotics commonly used to treat upper respiratory infections, e.g., penicillins, cephalosporins, sulfonamides, neosporin, polysporin, mupirocin, and the like. In humans, it can be less desirable to utilize penicillin derivatives due to allergic problems associated with their use. Examples of suitable antifungal agents include, but are not limited to miconazole, ketaconazole and the like. One of skill in the art can also appreciate that other natural antimicrobial agents can be utilized including but not limited to, e.g., pentisols such as xylitol. Antimicrobial, e.g., antibiotic selection and dosage can, of course, vary depending upon physician or veterinarian preference and the infectious agent to be treated and the desired therapeutic regimen.

Other agents which can be added to the core compositions of the invention include, cytokine modulators or inhibitors and/or antileukotrienes or leukotriene receptor antagonists. Examples of cytokine modulators can include pimecrolimus, tacrolimus, zileuton and the like. Examples of suitable leukotriene receptor antagonists include, but are not limited to montelukast sodium, and zafirulakast.

Cromolyn sodium (also known as sodium cromoglycate (SCG)) and/or pryanoquinolones such as, e.g., nedocromil sodium, and other mast cell stabilizers can also be added to the core compositions set forth herein. Likewise, in certain instances, non-steroidal anti-inflammatory agents such as, e.g., acetaminophen, ibuprofen, ketofen and/or Cox-2 inhibitors such as, e.g., rofecoxib or celecoxib can be added to the core compositions of the invention. To further reduce inflammation and in certain embodiments these NDAID agents can be used in place of corticosteroid agents in the core formulations. Anti-serotonin agents can also be utilized as an adjunct to the core formulations.

In another embodiment, the invention provides a method for the non-addictive treatment and/or prevention of allergic, non-allergic and/or mixed rhinitis comprised of administering a therapeutic and/or a preventative amount of a composition comprised of a suitable nasal decongestant; a suitable synthetic or non-synthetic corticosteroid; and a suitable anticholinergic agent. In a presently preferred embodiment, the method comprises the intranasal administration of the compositions set forth herein. Depending upon the severity of the rhinitic condition, the compositions can be administered 1×/day or 2×/day or as needed for symptomatic relief.

In a presently preferred therapeutic regimen for treatment of rhinitis, e.g., mixed rhinitis, the compositions of the invention can be administered, e.g., as an intranasal spray, in a split dosage fashion wherein a first treatment can be administered to relieve the acute nasal congestion and decrease swelling of nasal passages. The first administration is followed up by a second administration of the nasal spray at a preselected time after the first administration to provide a more long term and effective relief of the mixed rhinitis being treated. For example, a first administration of the composition is administered to the subject and a second administration is followed at between about 5 and about 45 minutes but preferably at about 10-15 minutes following the first administration. This split dosage regimen can be repeated daily or 2×/day or as needed to control or provide symptomatic relief of the rhinitic condition being treated.

Example Of A Presently Preferred Embodiment: A Novel Composition for the Treatment of Allergy Symptoms: Allergy-Sinus Total Coverage Nasal Spray An Allergy-Sinus "Total Control" Nasal Spray composition is provided which is comprised of:

1. 2.0 cc of 0.05% Oxymetazoline HCl with Q/S Camphor &/or
    Q/S Eucalyptol &/or
    Q/S Menthol for desired Aromatic Cooling Affect
    (the volume, and thus the concentration of Oxymetazoline Hcl in the final composition can range from about 0.25 cc to about 4 cc of a 0.05% solution);
2. 5 cc Ipratropium Bromide @ 42 meq/0.1 cc
    (the volume, and thus the concentration oflpratropium Bromide in the final composition can range from about 1.25 cc to about 12 cc of a 42 meq/0.1 cc solution); and
3. Add only one of the items listed below:
    i. 6 cc of 0.25 gm/cc Triamcinolone Acetate with buffers, stabilizers & surfactants (the volume, and thus the concentration of Triamcinolone Acetate in the final composition can range from about 3 cc to about 24 cc of a 0.25 gm/cc solution);
    ii. 6 cc of Betamethasone Dipropionate @ 84 meq/0.1 cc with buffers, stabilizers & surfactants (the volume, and thus the concentration of Betamethasone Dipropionate in the final composition can range from about 3 cc to about 24 cc of a 84 meq/0.1 cc solution);
    iii. 5 cc Budesonide 384 meq/cc with buffers, stabilizers & surfactants (the volume, and thus the concentration of Budesonide in the final composition can range from about 3 cc to about 24 cc of a 384 meq/cc solution);
    iv. 11 cc Flunisolide in 0.025% solution with buffers, stabilizers & surfactants (the volume, and thus the concentration of Flunisolide in the final composition can range from about 3 cc to about 24 cc of a 0.025% solution);
    v. 10 cc Fluticasone Propionate @ solution to allow 100 meq per 0.10 cc (the volume, and thus the concentration of Fluticasone Propionate in the final composition can range from about 3 cc to about 24 cc of a 100 meq per 0.10 cc solution);
    vi. 10 grams of 0.05% Mometasone Furoate Monohydrate to allow 100 meq per 0.10 cc (the volume, and thus the concentration of Mometasone Furoate Monohydrate in the final composition can range from about 5 cc to about 40 cc of a of 0.05% Mometasone Furoate Monohydrate solution at 100 meq per 0.10 cc).

Optional:
4. 5 cc Azelastine HCl in a 0.1% solution (0.137 mg) an antihistamine helpful for extra allergy and vasomotor rhinitis control can be added (the volume, and thus the concentration of Azelastine HCl in the final composition can range from about 1.25 cc to about 7.5 cc of a of 0.1% Azelastine HCl solution).

The above composition, for example, can be useful for the methods of treatment and or prevention of upper respiratory conditions in man and in animals provided herein. However, it can be appreciated by one of skill in the art that other of the embodiments provided by the invention are, likewise, useful in the methods set forth herein. For example, in one embodiment the invention provides a composition useful in a method for the non-addictive treatment and/or prevention of an upper airway condition in a subject, comprising administering to the subject a composition comprising effective amounts of a suitable nasal decongestant; a suitable corticosteroid; and a suitable anticholinergic agent. The subject can be a human or animal subject and the upper airway condition can be, e.g., rhinitis (allergic, non-allergic and mixed) in man or pharyngitis in horses. The compositions set forth herein are also useful in methods of treatment of other upper respiratory and respiratory conditions, e.g., for treatment of inflammatory airway disease, heaves, guttural pouch inflammation and/or infection and sinusitis in horses.

In one embodiment, the compositions of the invention are adapted for intranasal administration such as via spraying, misting, or other direct topical application to the membranes or the compositions can be adapted for inhalation via a metered dose inhalation device or nebulization of the composition. The condition being treated, will likely dictate the choice of administration. For example, in humans suffering from mixed rhinitis, the compositions can be administered by a metered dose inhaler or spray or mist intranasal applicator. Whereas, in a horse, for example, the route of administration for pharyngitis can be via direct topical administration of the composition to the oropharynx via the use of a catheter (e.g., a canine urinary catheter or the like) or nasal cannula that is passed up the nasal passages such that the tip of the catheter or cannula is adjacent the target pharyngeal tissue and the composition is sprayed on topically. If, for example, the condition being treated is an inflamed guttural pouch, the catheter can be passed into the opening of the guttural pouch and the composition delivered directly into the pouch such that the membranous lining of the pouch is treated. Likewise, for IAD or heaves, nebulization or a commercially available inhaler can be employed. Examples of metered dose inhalers include the Equine AeroMask (Canadian Monaghan, Ontario, Canada) or the Equine Haler (Equine Healthcare APS, Hillerod, Denmark).

The frequency of administration for the methods set forth herein will, of course, vary according to the subject being treated, the condition and severity of the condition being treated and the particular combination of active agents within the composition. Given the teachings set forth herein and elsewhere, the skilled artisan will be able to tailor a therapeutic regimen suited to the individual being treated.

As set forth above, in one embodiment of the compositions of the invention, the suitable nasal decongestant is oxymetazoline hydrochloride and the effective amount of is oxymetazoline hydrochloride is from between about 0.25 ml to about 4.0 ml of a 0.05% solution of oxymetazoline hydrochloride.

Most preferably, the effective amount of is oxymetazoline hydrochloride is about 2.0 ml of a 0.05% solution of oxymetazoline hydrochloride added to the composition.

Any of a number of suitable corticosteriods can be utilized in the compositions of the invention. For example, in another embodiment, the suitable corticosteroid is triamcinolone acetate and the effective amount of triamcinolone acetate is from between about 3.0 ml to about 24.0 ml of a 0.25 gram/ml solution of triamcinolone acetate. Most preferably, the effective amount of triamcinolone acetate is about 6.0 ml of a 0.25 gram/ml solution of triamcinolone acetate added to the composition.

In yet another embodiment, the suitable corticosteroid of the composition is betamethasone dipropionate and the effective amount of betamethasone dipropionate is from between about 3.0 ml to about 24.0 ml of a 84 meq/0.1 ml solution of betamethasone dipropionate. More preferably, the effective amount of betamethasone dipropionate is about 6 ml of a 84 meq/0.1 ml solution of beta met has one dipropionate added to the composition. In still another embodiment, the suitable corticosteroid is budesonide and the effective amount of budesonide is from between about 3.0 ml to about 24.0 ml of a 384 meq/ml solution of budesonide, but, most preferably, the effective amount of budesonide is about 5 ml of a 384 meq/ml solution of budesonide added to the composition. Still another embodiment of the compositions of the invention comprises the utilization of flunisolide as the suitable corticosteroid and the effective amount of flunisolide is from between about 3.0 ml to about 24.0 ml of a 0.025% solution of flunisolide, but, more preferably the effective amount of flunisolide is about 11 ml of a 0.025% solution of flunisolide added to the composition.

In one embodiment, the suitable corticosteroid is fluticasone propionate and the effective amount of fluticasone propionate is from between about 3.0 ml to about 24.0 ml of a 100 meq/ml solution of fluticasone propionate. More preferably, the effective amount of fluticasone propionate is about 10 ml of a fluticasone propionate solution such that the final concentration of fluticasone propionate in the composition is about 100 meq/0.10 ml. In another embodiment, the suitable corticosteroid is mometasone furoate monohydrate and the effective amount of mometasone furoate monohydrate is from between about 5.0 ml to about 40.0 ml of a 0.05% solution of mometasone furoate monohydrate. Preferably the effective amount of mometasone furoate monohydrate is about 10 ml of a 0.05% solution of mometasone furoate monohydrate such that the final concentration of mom etas one furoate monohydrate in the composition is about 100 meq/0.10 ml. One of skill in the art can appreciate that the effective amount of corticosteroid will vary depending upon the choice of corticosteroid, the subject and condition being treated and the severity of the condition and the like. Given the teachings she forth herein, the effective amounts and dosage can be optimized by one of skill in the art.

In another embodiment, the suitable anticholinegic agent is ipratropium bromide and the effective amount of ipratropium bromide in the composition is from between about 1.25 ml to about 12.0 ml of a 42 meq/ml solution of ipratropium bromide, but, more preferably the effective amount of ipratropium bromide is about 5 ml of a 42 meq/ml solution of ipratropium bromide added to the composition. In a presently preferred embodiment, the compositions of the invention can further comprise an effective amount of suitable antihistamine such as, e.g., an antihistamine selected from the group consisting of cetirizine, chlorpheniramine, diphenhydramine, dexchlorpheniramine, astemizole, azelastine hydrochloride, acrivastine, loratadine, terfenadine, cyproheptidine or a combination thereof. In one preferred embodiment, the suitable antihistamine is azelastine hydrochloride and the effective amount of azelastine hydrochloride is from between about 1.25 ml to about 7.5 ml of a 0.1% solution of azelastine hydrochloride added to the composition. More preferably, the effective amount of azelastine hydrochloride is about 5 ml of a 0.1% solution of azelastine hydrochloride added to the composition.

Contained herein are several citations to literature references, the contents of which are hereby incorporated herein in their entirety by reference. The foregoing descriptions of novel and preferred embodiments of the invention have been presented for purposes of illustration and description. The descriptions are not intended to be exhaustive or to limit the invention to the precise form disclosed. Obvious modifications or variations are possible in light of the above testing. The embodiment was chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the claims made in this application when interpreted in accordance with the breadth to which they are fairly, legally and equitably entitled.

What is claimed is:

1. A method for the non-addictive treatment of rhinitis in a subject comprising administering to the subject an effective amount of a composition consisting essentially about 1 part to about 2 parts of 0.05% solution of oxymetazoline hydrochloride;

about 4 parts to about 6 parts of 0.25 gram/ml of triamcinolone acetate; and about 4 parts to about 6 parts 42 meq/0.1 ml solution of ipratropium bromide, wherein the subject is in need of treatment of rhinitis, and wherein the composition can be used on a long term basis without the subject developing an addiction to the composition.

2. The method of claim 1, wherein the composition consists essentially of:

about 2 parts of 0.05% solution of a oxymetazoline hydrochloride;

about 6 parts of 0.25 gram/ml of triamcinolone acetate; and about 5 parts 42 meq/0.1 ml solution of ipratropium bromide.

3. The method of claim 2, wherein the rhinitis is selected from the group consisting of allergic rhinitis, non-allergic rhinitis, and mixed rhinitis.

4. The method of claim 3, wherein the rhinitis is mixed rhinitis.

5. The method of claim 3, wherein the rhinitis is non-allergic rhinitis.

6. The method of claim 3, wherein the rhinitis is allergic rhinitis.

7. A method for the non-addictive treatment of rhinitis in a subject comprising administering to the subject an effective amount of a composition consisting essentially of effective amounts of about 1 part to about 4 parts of 0.05% solution of a oxymetazoline hydrochloride;

about 4 parts to about 6 parts of 0.25 gram/ml of triamcinolone acetate;

about 4 parts to about 6 parts 42 meq/0.1 ml solution of ipratropium bromide; and a suitable antihistamine selected from the group consisting of cetirizine, chlorpheniramine, diphenhydramine, dexchloropheniramine, astemizole, azelastine hydrochloride, acrivastine, loratadine, terfenadine, cyproheptidine and combinations thereof, wherein the subject is in need of treatment of rhinitis, and wherein the composition can be used on a long term basis without the subject developing an addiction to the composition.

8. The method of claim 7, wherein the suitable antihistamine is about 1.25 parts to about 7.5 parts of a 0.1% solution of azelastine hydrochloride.

9. The method of claim 8, wherein the suitable antihistamine is about 5 ml of a 0.1% solution of azelastine hydrochloride.

10. A method for the non-addictive treatment of rhinitis in a subject comprising administering to the subject an effective amount of a composition consisting essentially of effective amounts of
about 1 part to about 4 parts of 0.05% solution of a oxymetazoline hydrochloride;
about 4 parts to about 6 parts of 0.25 gram/ml of triamcinolone acetate;
about 4 parts to about 6 parts 42 meq/0.1 ml solution of ipratropium bromide; and a suitable antileukotriene or a leukotriene receptor antagonist.

11. A method for the non-addictive treatment of rhinitis in a subject comprising administering to the subject an effective amount of a composition consisting essentially of effective amounts of
about 1 part to about 4 parts of 0.05% solution of a oxymetazoline hydrochloride;
about 4 parts to about 6 parts of 0.25 gram/ml of triamcinolone acetate;
about 4 parts to about 6 parts 42 meq/0.1 ml solution of ipratropium bromide; and a suitable aromatic agent.

12. The method of claim 11, wherein the suitable aromatic agent is selected from the group consisting of camphor, menthol, eucalyptus and combinations thereof.

13. A method for the non-addictive treatment of rhinitis comprising:
identifying a subject in need of treatment of rhinitis; and
administering intranasally to the subject an effective amount of a composition comprised of about 2 parts of 0.05% solution of oxymetazoline hydrochloride; about 6 parts of 0.25 gram/ml of triamcinolone acetate; and about 5 parts 42 meq/0.1 ml solution of ipratropium bromide, wherein the administering occurs on a long term basis without the subject developing an addiction to the oxymetazoline hydrochloride nasal decongestant.

14. A method for the non-addictive treatment of chronic rhinitis comprising:
identifying a subject in need of treatment of chronic rhinitis; and
administering intranasally to the subject an effective amount of a composition comprised of about 1 part to about 4 parts of 0.05% solution of oxymetazoline hydrochloride; about 4 parts to about 6 parts of 0.25 gram/ml of triamcinolone acetate; and about 4 parts to about 6 parts 42 meq/0.1 ml solution of ipratropium bromide, wherein the administering occurs on a long term basis without the subject developing an addiction to the oxymetazoline hydrochloride nasal decongestant.

15. The method of claim 14, wherein the identified subject is addicted to a nasal decongestant.

16. A method for the non-addictive treatment of rhinitis in a subject comprising administering to the subject an effective amount of a composition consisting essentially of:
about 0.25 part to about 4 parts of 0.05% solution of oxymetazoline hydrochloride;
about 1.25 parts to about 12 parts of ipratropium bromide; and
about 3 parts to about 24 parts of a corticosteroid selected from the group consisting of a 0.25 gram/ml solution of triamcinolone acetate, a 84 meq/0.1 ml solution of betamethasone dipropionate, a 384 meq/ml solution of budesonide, a 0.025% solution of flunisolide, a 100 meq/ml solution of fluticasone propionate, and a 0.05% solution of mometasone furonate monohydrate; wherein the subject is in need of treatment of rhinitis, and wherein the composition can be used on a long term basis without the subject developing an addiction to the composition.

17. The method of claim 16, wherein the composition consists essentially of:
about 2 parts of 0.05% solution of oxymetazoline hydrochloride; about 5 parts of ipratropium bromide; and a corticosteroid selected from the group consisting of about 6 parts of a 0.25 gram/ml solution of triamcinolone acetate, about 6 parts of a 84 meq/0.1 ml solution of betamethasone dipropionate, about 5 parts of a 384 meq/ml solution of budesonide, about 11 parts of a 0.025% solution of flunisolide, about 10 parts of a 100 meq/ml solution of fluticasone propionate, and about 10 parts of a 0.05% solution of mometasone furonate monohydrate; wherein the subject is in need of treatment of rhinitis, and wherein the composition can be used on a long term basis without the subject developing an addiction to the composition.

18. A method for the non-addictive treatment of rhinitis in a subject comprising administering to the subject an effective amount of a composition consisting essentially of:
about 0.25 part to about 4 parts of 0.05% solution of oxymetazoline hydrochloride;
about 1.25 parts to about 12 parts of ipratropium bromide;
about 3 parts to about 24 parts of a corticosteroid selected from the group consisting of a 0.25 gram/ml solution of triamcinolone acetate, a 84 meq/0.1 ml solution of betamethasone dipropionate, a 384 meq/ml solution of budesonide, a 0.025% solution of flunisolide, a 100 meq/ml solution of fluticasone propionate, and a 0.05% solution of mometasone furonate monohydrate;
a suitable antihistamine selected from the group consisting of cetirizine, chlorpheniramine, diphenhydramine, dexchloropheniramine, astemizole, azelastine hydrochloride, acrivastine, loratadine, terfenadine, cyproheptidine and combinations thereof, wherein the subject is in need of treatment of rhinitis; and
a suitable aromatic agent,
wherein the subject is in need of treatment of rhinitis, and wherein the composition can be used on a long term basis without the subject developing an addiction to the composition.

19. The method of claim 18, wherein the suitable antihistamine is about 1.25 parts to about 7.5 parts of a 0.1% solution of azelastine hydrochloride.

20. The method of claim 19, wherein the suitable antihistamine is about 5 ml of a 0.1% solution of azelastine hydrochloride.

21. The method of claim 19, wherein the suitable aromatic agent is selected from the group consisting of camphor, menthol, eucalyptus and combinations thereof.

22. A method for the non-addictive treatment of rhinitis in a subject comprising administering to the subject an effective amount of a composition consisting essentially of:
about 0.25 part to about 4 parts of 0.05% solution of oxymetazoline hydrochloride;
about 1.25 parts to about 12 parts of ipratropium bromide;

about 3 parts to about 24 parts of a 0.25 gram/ml solution of triamcinolone acetate;

a suitable antihistamine selected from the group consisting of cetirizine, chlorpheniramine, diphenhydramine, dexchlorpheniramine, astemizole, azelastine hydrochloride, acrivastine, loratadine, terfenadine, cyproheptidine and combinations thereof, wherein the subject is in need of treatment of rhinitis; and a suitable aromatic agent, wherein the subject is in need of treatment of rhinitis, and wherein the composition can be used on a long term basis without the subject developing an addiction to the composition.

23. The method of claim 22, wherein the suitable antihistamine is about 1.25 parts to about 7.5 parts of a 0.1% solution of azelastine hydrochloride.

24. The method of claim 22, wherein the suitable antihistamine is about 5 ml of a 0.1% solution of azelastine hydrochloride.

25. The method of claim 22, wherein the suitable aromatic agent is selected from the group consisting of camphor, menthol, eucalyptus, and combinations thereof.

26. A method for the non-addictive treatment of rhinitis in a subject comprising administering to the subject an effective amount of a composition consisting essentially of:

about 2 parts of 0.05% solution of oxymetazoline hydrochloride;

about 5 parts of ipratropium bromide;

about 6 parts of a 0.25 gram/ml solution of triamcinolone acetate;

a suitable antihistamine selected from the group consisting of cetirizine, chlorpheniramine, diphenhydramine, dexchlorpheniramine, astemizole, azelastine hydrochloride, acrivastine, loratadine, terfenadine, cyproheptidine and combinations thereof, wherein the subject is in need of treatment of rhinitis; and a suitable aromatic agent, selected from the group consisting of camphor, menthol, eucalyptus, and combinations thereof, wherein the subject is in need of treatment of rhinitis, and wherein the composition can be used on a long term basis without the subject developing an addiction to the composition.

* * * * *

UNITED STATES PATENT AND TRADEMARK OFFICE
CERTIFICATE OF CORRECTION

PATENT NO. : 7,867,508 B1
APPLICATION NO. : 11/829119
DATED : January 11, 2011
INVENTOR(S) : C. Steven Smith It is certified that error appears in the above-identified patent and that said Letters Patent is hereby corrected as shown below:

In claim 1, col. 12, line 30: Add the word "of" at the end of the line after "consisting essentially"

Signed and Sealed this
Eighth Day of March, 2011

David J. Kappos
*Director of the United States Patent and Trademark Office*